(12) United States Patent
Hsu et al.

(10) Patent No.: US 8,461,108 B2
(45) Date of Patent: Jun. 11, 2013

(54) SUBDERMAL TISSUE REMODELING USING MYOSTATIN, METHODS AND RELATED SYSTEMS

(75) Inventors: Michael Hsu, Oakland, CA (US); Lisa Elkins, Woodside, CA (US)

(73) Assignee: MyoScience, Inc., Redwood City, CA (US)

( * ) Notice: Subject to any disclaimer, the term of this patent is extended or adjusted under 35 U.S.C. 154(b) by 748 days.

(21) Appl. No.: 12/400,698

(22) Filed: Mar. 9, 2009

(65) Prior Publication Data

US 2009/0226424 A1 Sep. 10, 2009

Related U.S. Application Data

(60) Provisional application No. 61/034,781, filed on Mar. 7, 2008.

(51) Int. Cl.
*A61K 38/16* (2006.01)
*A61K 38/17* (2006.01)
*A61K 38/18* (2006.01)

(52) U.S. Cl.
USPC ........... 514/7.6; 514/8.9; 514/12.1; 514/18.6; 514/18.8

(58) Field of Classification Search
None
See application file for complete search history.

(56) References Cited

U.S. PATENT DOCUMENTS

| | | |
|---|---|---|
| 7,179,884 B2 | 2/2007 | Lee et al. |
| 2002/0157126 A1 | 10/2002 | Lee et al. |
| 2005/0208075 A1* | 9/2005 | Borodic ............... 424/239.1 |
| 2007/0129714 A1* | 6/2007 | Elkins et al. ............ 606/21 |
| 2007/0275895 A1 | 11/2007 | Duan et al. |
| 2008/0208179 A1* | 8/2008 | Chan et al. ............... 606/9 |

OTHER PUBLICATIONS

Zimmers et al. (2002, Science 296:1486-1488).*
U.S. Appl. No. 11/387,643, filed Mar. 23, 2006, Inventor: John A. Nowak (now abandoned).
Carlson et al., "Skeletal muscle myostatin mRNA expression is fiber-type specific and increases during hindlimb unloading," *Am. J. Physiol.* 277: R601-606 (1999).
Carruthers et al., "Botulinum A exotoxin use in clinical dermatology," *J. Am. Acad. Dermatol.* 34:788-796 (1996).
Cohn et al., "Myostatin does not regulate cardiac hypertrophy or fibrosis," *Neuromuscul. Disord.* 17: 290-296 (2007).
Derynck and Zhang, "Smad-dependent and Smad-independent pathways in TGF-beta family signaling," *Nature* 425: 577-584 (2003).
Durieux et al., "Ectopic expression of myostatin induces atrophy of adult skeletal muscle by decreasing muscle gene expression," *Endocrinology* 148: 3140-3147 (2007).
Gonzalez-Cadavid et al., "Organization of the human myostatin gene and expression in healthy men and HIV-infected men with muscle wasting," *Proc. Natl. Acad. Sci. U.S.A.* 95: 14938-14943 (1998).
Lee and McPherron, "Regulation of myostatin activity and muscle growth," *Proc. Natl. Acad. Sci. U.S.A.* 98: 9306-9311 (2001).
Lee et al. "Regulation of muscle growth by multiple ligands signaling through activin type II receptors," *Proc. Natl. Acad. Sci. U.S.A.* 102: 18117-18122 (2005).
McCroskery et al., "Myostatin negatively regulates satellite cell activation and self-renewal," *J. Cell. Biol.* 162: 1135-1147 (2003).
McPherron and Lee, "Double muscling in cattle due to mutations in the myostatin gene," *Proc. Natl. Acad. Sci. U.S.A.* 94: 12457-61 (1997).
Thomas et al. "Myostatin, a negative regulator of muscle growth, functions by inhibiting myoblast proliferation," *J. Biol. Chem.* 275: 40235-40243 (2000).
Wehling et al., "Modulation of myostatin expression during modified muscle use," *Faseb J.* 14: 103-110 (2000).
Zhu et al., "Relationships between transforming growth factor-beta1, myostatin, and decorin: implications for skeletal muscle fibrosis," *J. Biol. Chem.* 282: 25852-25863 (2007).
International Preliminary Report on Patentability, PCT Application No. PCT/US2009/036559, dated Sep. 7, 2010, 8 pages.

* cited by examiner

*Primary Examiner* — Elizabeth C Kemmerer
(74) *Attorney, Agent, or Firm* — Kilpatrick Townsend and Stockton LLP (57) ABSTRACT

Systems and methods of tissue remodeling or altering a surface of a skin of a patient are provided. A method includes increasing myostatin activity in a target tissue. Methods can include increasing myostatin activity in a target tissue in addition to various tissue remodeling techniques, including cryogenic cooling of target tissue for tissue remodeling.

22 Claims, 8 Drawing Sheets

SUBDERMAL TISSUE REMODELING USING MYOSTATIN, METHODS AND RELATED SYSTEMS

CROSS-REFERENCE TO RELATED APPLICATION

The present invention claims the benefit of priority under 35 U.S.C. § 119(e) of U.S. Provisional Application No. 61/034,781, filed Mar. 7, 2008 (Attorney Docket No. 025917-000900US), the entire content of which is incorporated herein by reference.

BACKGROUND OF THE INVENTION

The present invention is generally directed to medical devices, systems, and methods, particularly for improving the appearance of a patient and other applications, including applications cosmetic in nature. Embodiments of the invention include devices, systems, and methods for increasing myostatin activity in subcutaneous tissues so as to selectively remodel one or more target tissues and alter an exposed surface of the skin, often inhibiting undesirable and/or unsightly effects on the skin (such as lines, wrinkles, or cellulite dimples) or on other surrounding tissue. The remodeling of the target tissue may achieve a desired change in its behavior or composition, and will often help alleviate cosmetically undesirable characteristics.

The desire to reshape various features of the human body to either correct a deformity or merely to enhance one's appearance is common. This is evidenced by the growing volume of cosmetic surgery procedures that are performed annually. Many procedures are intended to change the surface appearance of the skin by reducing lines and wrinkles. Some of these procedures involve injecting fillers or stimulating collagen production.

More recently, pharmacologically based therapies for wrinkle alleviation and other cosmetic applications have gained in popularity. Botulinum toxin type A (BOTOX®) is an example of a pharmacologically based therapy used for cosmetic applications. It is typically injected into the facial muscles to block muscle contraction, resulting in temporary denervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing, e.g., via collagen enhancement; or enhancement can also be achieved via collagen or other injectable. Development of non-pharmacologically based cosmetic treatments also continues. For example, endermology is a mechanical based therapy that utilizes vacuum suction to stretch or loosen fibrous connective tissues which are implicated in the dimpled appearance of cellulite. Other examples include transdermal ultrasound, which is used to reduce fat mass, and several types of energy (e.g., RF) used to promote collagen building and skin tightening. While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like.

In light of the above, it would be desirable to provide improved medical devices, systems, and methods, particularly for treatment of wrinkles, fat, cellulite, and other cosmetic defects, as well as some other effects such as treatment of lesions (e.g., malignant, benign, etc.), acute or chronic pain, etc. It would be particularly desirable if these new techniques provided an alternative visual appearance improvement and/or treatment mechanism which could replace and/or compliment known bioactive and other cosmetic therapies, ideally allowing patients to decrease or eliminate the injection of toxins and harmful cocktails or pharmaceuticals while providing similar or improved cosmetic results. It would also be desirable if such techniques were performed percutaneously using only local or no anesthetic with minimal or no cutting of the skin, no need for suturing or other closure methods, no extensive bandaging, and limited or no bruising or other factors contributing to extended recovery or patient "down time".

BRIEF SUMMARY OF THE INVENTION

The present invention generally provides improved medical devices, systems, and methods for the treatment of cosmetic and other defects, including those defects that are due at least partially to muscle activity or contraction in a tissue. The current invention is based at least partially on the discovery that activation of myostatin activity in a target tissue can be used to inhibit muscle contractility and/or mass in that tissue and alleviate or treat certain defects associated with muscle activity and contraction, including certain cosmetic defects such as skin lines or wrinkles. Embodiments of the present invention include increasing myostatin activity in a target tissue, such as by delivering a functionally active myostatin peptide to the tissue, so as to aid in the reduction of muscle contractility and/or mass, and alleviating certain defects such as surface cosmetic defects, lines, wrinkles, or rhytids, and the like on the skin surface. Increasing myostatin activity according to the present invention can also be used in conjunction with other treatment techniques and methodologies, such as applying cooling to a tissue, and in some cases has been observed to prolong the cosmetic or therapeutic effects (e.g., muscle contractility/mass reducing effects) of a separately or co-administered treatment. Thus, embodiments of the present invention can include applying cooling to a tissue, e.g., with at least one probe inserted through an exposed surface of the skin of a patient. The cooling may remodel one or more target tissue so as to effect a desired change in a composition of the target tissue and/or a change in its behavior. Exemplary embodiments of the cooling treatments will interfere with the nerve/muscle contractile function chain so as to mitigate wrinkles of the skin, and related treatments may be used therapeutically for treatment of back and other muscle spasms, chronic pain, and the like. Some embodiments may remodel subcutaneous adipose tissue or fibrous connective tissue so as to alter a shape or appearance of the skin surface.

In one embodiment, for example, increasing myostatin activity according to the present methods can be accomplished in conjunction with application of cooling to a target tissue, and increasing of myostatin activity in the target tissue can enhance or increase the duration of the tissue remodeling effects of the cooling treatment. Examples of tissue cooling can include applying a cooling to a target tissue with at least one probe though an exposed surface of the skin of a patient, with the cooling being applied to tissue of the target below the skin and in some cases to the surface/skin itself. The cooling may remodel one or more target tissues so as to effect a desired change in a composition of the target tissue (e.g., reduced muscle mass) and/or a change in its behavior (e.g., altered muscle contractility). Cooling treatments can interfere with the nerve/muscle contractile function chain and mitigate lines and wrinkles of the skin, and related treatments can be used for other treatment endpoints, such as treatment for muscle spasms, back spasms, chronic pain, and the like. In many cases, prior to remodeling, the skin surface will undesirable cosmetic features such as lines or wrinkles. Contraction of muscles in the target tissue, e.g., sub-dermal muscles, and associated movement of the skin may contribute to the development and appearance of these lines or wrinkles, and the remodeling can be performed so as to reduce or eliminate this contraction and/or movement, effectively smoothing the lines or wrinkles. The skin surface will often include a region of the face, with target tissues optionally comprising muscle, nerve, connective tissue nerve/muscle junction, and/or the like associated with muscle in a target region. The line/wrinkle alleviation treatment, such as the cooling described herein, can inhibit contraction of the muscle and/or reduce muscle mass so as to improve the appearance of the patient. Further increasing of myostatin activity in the target tissue as either a separate step (e.g., delivery of myostatin before or after cooling) or together with cooling can inhibit myogenesis in the target tissue, and can increase the effectiveness and duration of the treatment applied.

Thus, in one aspect of the present invention, a method is provided for inhibiting myogenesis in a target tissue, which can inhibit muscle function (e.g., contractility) and/or mass of the target tissue and alter a surface of a skin of a patient. The method can include increasing myostatin activity in the target tissue so as to inhibit myogenesis in the target tissue and inhibit contraction of muscle in the target tissue and/or reduction in muscle mass, and an alteration in the surface of the patient's skin. Inhibition of muscle contraction by increased myostatin activity may occur indirectly, e.g., where lack of myofibers in the muscle following agent delivery could result in at least partially reduced muscle contraction. In some embodiments, inhibiting myogenesis according to the present invention can be provided in addition to or in conjunction with other tissue remodeling treatments, such as skin smoothing or wrinkle reduction treatments, such as cryogenic cooling techniques, radiofrequency (RF) energy delivery, delivery of pharmaceutical agents, botulinum toxin (e.g., BOTOX™) treatment, surgical methods, or combinations thereof.

In another aspect, the present invention can include a method of treating (e.g., cosmetically treating) a target tissue of a patient. Such a method can include cooling the target tissue, e.g., below the skin surface, such that the cooling of the target tissue inhibits muscle contractility in the target tissue and/or alters a shape of the skin surface. The method can further include delivering to the target tissue myostatin or an agent that increases myostatin activity in the target tissue. Cooling can be selected to induce muscle damage or otherwise decrease/inhibit muscle contractility in the target tissue, with increased myostatin activity in the target tissue inhibiting myogenesis in the target tissue and increasing repair time of the muscle and augmenting/increasing the duration of certain effects of the cooling treatment (e.g., skin smoothing, wrinkle alleviation, reduction)

In another aspect, the present invention can include a method of increasing a duration of a treatment, such as a skin smoothing treatment, cosmetic treatment, or wrinkle alleviation technique, including techniques that include tissue remodeling or inhibiting muscle contractility in a target tissue so as to effect a skin surface. Such a method can include providing a first treatment (e.g., skin smoothing) and delivering a myostatin activity increasing agent to the target tissue so as to inhibit myogenesis in the target tissue. The increased myostatin activity can further augment wrinkle reduction of cosmetic effects of the treatment or increase the duration of the skin smoothing compared to delivery of the skin smoothing treatment in the absence of the increased myostatin activity.

In yet another aspect, the present invention provides systems and devices. In one embodiment, a system for altering a surface of a skin of a patient is provided. The system can include a tissue cooling unit for delivering cooling to a target tissue and a myostatin agent delivery unit for delivering myostatin or a myostatin activity increasing agent to the target tissue.

In some embodiments, the skin surface may have an uneven cellulite or other adipose tissue-induced texture and/or shape. The remodeling may be performed so as to smooth such a texture so as to improve the appearance of the patient. Optionally, the cooling may be performed so as to induce a reduction in tissue mass, e.g., after removal of the probe from the patient. The reduction in tissue mass may occur as part of a tissue response to the cooling, optionally as part of the healing process, and the reduction in tissue mass may at least help provide a desired change in the shape of the skin surface. For example, where the tissue comprises an adipose tissue, a healing response to the cooling may decrease a mass of the adipose tissue by inducing adipose tissue restoration. In other embodiments, the cooling may reduce muscle mass, particularly of muscles of the face which are associated with lines and wrinkles.

For embodiments including tissue cooling, in general, the target tissue may be cooled to a temperature from about 10° C. to about −40° C., with the target tissue optionally being cooled to a temperature in a range from about 0° C. to about −15° C., as well as temperatures below about −15° C., including a temperature in a range from about 0° C. to about −20° C. More moderate treatment temperatures (for example, warmer than about −5° C.) and briefer treatment times may provide temporary efficacy, while colder treatment temperatures (for example, at about −5° C. or cooler) and longer treatment times may result in permanent changes to the target tissue and/or skin surface shape. Surprisingly, within some treatment temperature ranges, warmer treatments may provide more long-term or even permanent efficacy, while colder treatment temperatures may result in temporary changes to the target tissue and skin surface shape. For example, in some embodiments long-term or permanent efficacy of the treatment may be provided through apoptosis (sometimes referred to as programmed cell death). In contrast, necrosis-based effects may be reduced or eliminated with healing. Apoptosis can reduce muscle mass or disrupt the chain of contractility without inducing inflammation and triggering of the satellite cells that may be involved in the skeletal muscle repair process. Alternative mechanisms may also be involved, including a temporary and/or permanent loss of elasticity in muscle tissues through changes in morphology of collagen and/or elastin with ice formation, necrosis, a loss of elasticity in the fibrous connective tissue, impairment of signal transmission along the neural pathways, blocking production of acetylcholine (or other chemicals pertinent to contractility) or disrupting conductivity, hypoxia (optionally by cutting-off of the blood supply to a muscle or other tissue in the contractile chain through apoptosis or some other mechanism), or the like.

In yet another method aspect, the invention provides a method for treating a patient. The patient has a skin surface and a muscle therebelow. The method comprises directing sufficient tissue remodeling energy or cooling below the skin surface so that contraction of the muscle is inhibited or a loss of elasticity is induced. Related methods may comprise applying chemicals, and/or a means of cutting-off the tissue's blood supply.

Along with directing of cooling to (for example) a component of the contractile chain of a muscle, embodiments of the invention may rely at least in part on any of a variety of forms of energy transmissions to these or other tissues so as to inhibit muscle contraction, decrease muscle (or other tissue) mass, and the like. Suitable energy forms that may be used in place of or in conjunction with cooling may include ultrasound energy, radio frequency electrosurgical energy, microwave energy, laser energy, electromagnetic or particle radiation, and the like. Optionally, any of these treatment modalities may be combined with the use of bioactive agents, chemicals, or varied method of cutting off the tissue's blood supply.

Methods of the present invention can be directed to a variety of target tissues and are not limited to any particular tissue. Target tissues can typically include dermatological tissues and/or subcutaneous tissues. For example, a target tissue can include a patient's skin and/or tissue below the skin, or below an exterior surface of the skin. As set forth above, target tissues can include muscles or muscle containing tissues, nerves, blood vessels, as well as adipose tissues. Target tissues can also include various types of lesions, wounds, and the like, including, for example, various malignant (e.g., cancerous) or benign lesions, acne, warts, scar tissue, and the like.

In another embodiment, the cooling can be selected so as to induce a reduction in tissue mass, for example, during or proximate to the time of energy delivery or after removal of the probe from the patient. Reduction of tissue mass can include mass reduction of any type of tissue amenable to treatment according to the inventive methods described herein, including, for example, adipose tissue (e.g., macrosculpting/microsulpting fat), muscle tissue, skin tissue, tissue of a wound or lesion (e.g., benign lesion, malignant lesion, wart, scar tissue, acne, etc.), and the like. In yet another embodiment, delivery of the cooling energy can promote healing of the target tissue (e.g., lesion, wound, etc.).

In yet another aspect of the present invention, a method for treating a target tissue of a patient is provided. The method includes inserting a needle probe distally to penetrate into a target tissue of the patient, and directing a cooling energy into the target tissue through the probe so as to inhibit contraction of a muscle of the target tissue and remodel the target tissue. In some instances, delivery of the cooling energy to the target tissue can be accomplished using a non-penetrating probe. Thus, in another aspect, a method of treating a target tissue of a patient is provided, the method including positioning a non-penetrating probe in contact with a skin surface of the target tissue, and directing a cooling energy through the probe and into the target tissue so as to remodel the target tissue. Target tissues can include, for example, a lesion, such as an acne lesion.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

As set forth above, the present invention is based at least partially on the discovery that increasing myostatin activity in a target tissue can inhibit muscle contractility and/or mass in that tissue and alleviate or treat certain skin features, e.g., cosmetic features or defects, or defects associated with muscle activity and contraction, including certain skin surface alterations, lines or wrinkles As such, embodiments of the present invention include increasing myostatin activity in a target tissue so as to inhibit the process of myogenesis in the target tissue. Increasing myostatin activity can be accomplished by various methods, such as by delivering a functionally active myostatin peptide to the tissue, which will aid in the reduction of muscle contractility and/or mass. Such increased myostatin activity, according to the present invention, can alleviate certain defects such as surface cosmetic defects, lines, wrinkles, or rhytids, and the like on the skin surface. Increasing myostatin activity according to the present invention can be used in conjunction with other treatment techniques and methodologies, and in some cases has been observed to prolong the cosmetic or therapeutic effects (e.g., muscle contractility/mass reducing effects) of a separately or co-administered treatment.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles in combination with increasing myostatin activity, as described further herein.

Myostatin (also known as "Growth and Differentiation Factor 8", or GDF-8) is a muscle specific factor that inhibits the process of myogenesis and is associated with reduced muscle mass and various muscle wasting diseases. Myostatin is fairly well characterized in terms of activity, functionality, signaling pathways and mechanisms, associated phenotypes (e.g., reduced muscle mass, muscle wasting, etc.). However, the vast majority of research focus and development efforts for myostatin related therapies or treatments focus on inhibiting myostatin activity in order to increase muscle mass, reduce muscle wasting, and/or stimulate myogenesis. Few, if any, known techniques focus on actually increasing myostatin activity or deliberately inhibiting the process of myogenesis.

Myostatin is part of the transforming growth factor-β (TGF-β) superfamily, which is known to play an important role in proliferation, differentiation, and various other functions in most cell types during embryonic development and adult homeostasis. Like other TGF-β family members, myostatin is naturally synthesized in vivo as a precursor protein that undergoes proteolytic processing at a dibasic site to generate an N-terminal propeptide and a disulfide linked C-terminal dimer, which is the biologically active molecule. The circulating form of myostatin includes a latent complex of the myostatin C-terminal dimer and other proteins, including the myostatin propeptide, which inhibit the biological activity of the C-terminal dimer. (Lee S J and McPherron A C. Proc. Natl. Acad. Sci. U.S.A. 98: 9306-11 (2001)).

Myostatin decreases myogenesis, thereby decreasing muscle mass. Various muscle wasting ailments or diseases have been found to be related to increased levels of Myostatin. (Carlson CJ, Booth FW, Gordon SE. Am. J. Physiol. 277: R601-6 (1999); Gonzalez-Cadavid NF, Taylor WE, Yarasheski K, et al. Proc. Natl. Acad. Sci. U.S.A. 95: 14938-43 (1998); Wehling M, Cai B, Tidball JG., Faseb J. 14: 103-10 (2000)). Additionally, a distinct role of myostatin in muscle growth has been observed, including observations that increased myostatin activity decreases muscle mass and muscle fiber maintenance. A null mutation in the myostatin gene found in the cattle population was directly linked to a double muscling phenotype. (McPherron AC and Lee SJ. Proc. Natl. Acad. Sci. U.S.A. 94: 12457-61 (1997)). Muscle section analysis found that not only is there an increase in the number of muscle fibers, but also an increase in the size of the fibers. Recently a group has shown that ectopic expression of Myostatin can induce muscle reduced muscle mass. (Durieux AC, Amirouche A, Banzet S, et al. Endocrinology 148: 3140-3147 (2007)). Myostatin mechanisms of action are still being elucidated and may include inhibition of satellite cell activation, satellite cell renewal, myoblast proliferation, myoblast differentiation, and/or maintenance of muscle fiber. Numerous studies have shown that myostatin seems to cause muscle reduction at every step of myogenesis, including the maintenance of muscle fibers (Thomas M, Langley B, Berry C, et al. J. Biol. Chem. 275: 40235-43 (2000); Durieux AC, Amirouche A, Banzet S, et al. Endocrinology 148: 3140-3147 (2007); McCroskery S, Thomas M, Maxwell L, Sharma M, Kambadur R. J. Cell. Biol. 162: 1135-47 (2003)). It has also been shown that myostatin has a specific impact on skeletal muscle while leaving other muscle types, such as cardiac muscle unaffected (Cohn RD, Liang HY, Shetty R, Abraham T, Wagner KR. Neuromuscul. Disord. 17: 290-6 (2007)).

Investigations of the mechanism of how myostatin inhibits muscle growth have elucidated certain aspects of the myostatin signaling pathway and signaling mechanisms. For example, studies have shown that increasing levels of Follistatin can inhibit myostatin and increase myogenesis. Follistatin-related protein (FLRP) and follistatin are known to directly bind and inhibit myostatin and its receptor. (Zhu J, Li Y, Shen W, et al. J. Biol. Chem. 282: 25852-25863 (2007)). Also, myostatin has been show to inhibit cellular progression through the cell cycle and into the S phase of the cell cycle, particularly through upregulation of p21 expression (Cdk inhibitor) (Thomas M, Langley B, Berry C, et al. J. Biol. Chem. 275: 40235-43 (2000)). However, some details of the exact molecular mechanism that myostatin plays in myogenesis has yet to be elucidated.

Figure 1:
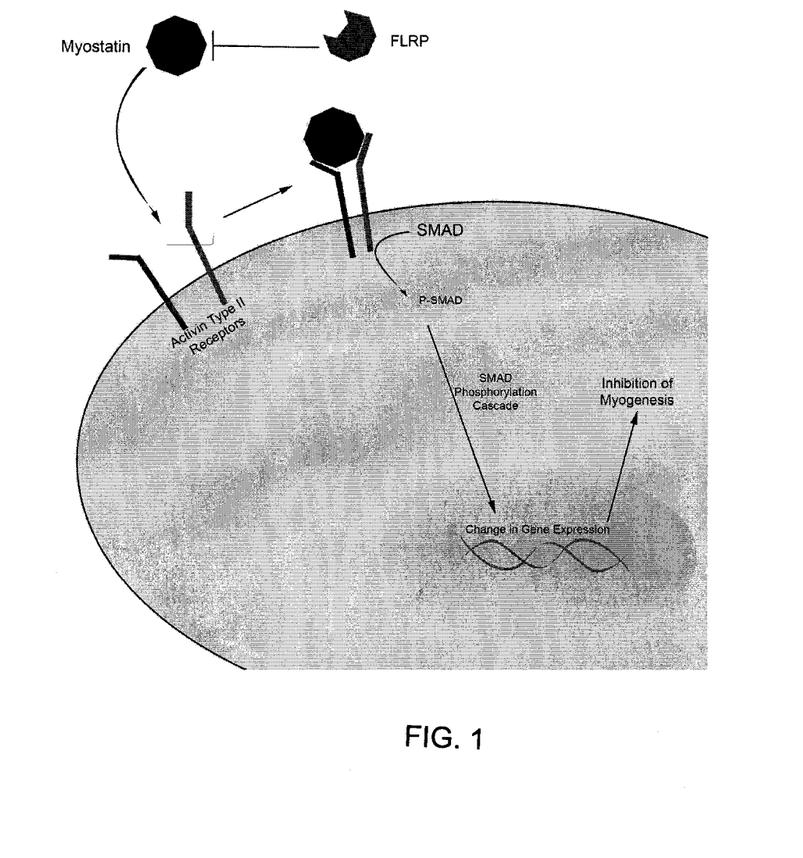
FIG. 1 is a signaling pathway graphic illustrating certain aspects of myostatin signaling.

In myostatin signaling, myostatin interacts with the ActR2A and ActR2B receptors (activin type II receptors) which leads to an overall inhibition of myogenesis of the cell (see FIG. 1). (Lee S J, Reed L A, Davies M V, et al. Proc. Natl. Acad. Sci. U.S.A. 102: 18117-22 (2005)). The main genes known to be affected by myostatin signaling are the myogenic regulatory factors (MRF), such as, for example, myogenin, MyoD, and Myf5. Additionally, there are at least 29 ligands that can signal 5 type II and 7 type I receptors in the TGF-β superfamily. Each ligand can recruit a unique combination of receptors that will signal a specific set of SMAD proteins in the cell. The effector SMAD proteins can then change gene expression via recognition of the SMAD binding element of the DNA. (Derynck R, Zhang Y E. Nature 425: 577-84 (2003)).

As mentioned above, there are various muscle wasting are related to increased myostatin activity. Such muscle wasting diseases include, e.g., muscular dystrophy, AIDS wasting syndrome, and some types of cancer. There are reported clinical trials on increasing the muscle mass of people who are suffering through a muscular dystrophy disease. Efforts to reduce muscle wasting include inhibiting the myostatin activity or signaling of myostatin. One method of inhibiting myostatin activity is by use myostatin blocking compounds, such as recombinant human antibodies that specifically bind to myostatin and inhibit the protein from signaling its receptor (Wyeth). Another reported approach is the use of a soluble form of the activin type II receptor (ACVR2B/Fc) to bind available myostatin in the environment. This is designed to effectively reduce the availability of myostatin to signal through the endogenously available activin type II receptor present on the cell membrane.

FIG. 1 illustrates certain basic aspects of myostatin signaling. Referring to FIG. 1, myostatin interacts with activin type II receptors at the cell surface. Once activated, the activin type II receptors will initiate the SMAD phosphorylation cascade. The final effector SMAD will result in a change in gene expression at the transcription level; therefore, leading to an inhibition of myogenesis. Follistatin or a follis regulates the amount of available myostatin for signaling by directly binding to myostatin. Increasing myostatin activity according to the present methods can include addressing and effecting myostatin signaling at any step along the myostatin signaling pathway.

Thus, the term "myostatin" refers to a specific growth and differentiation factor-8, as well known and described throughout the art, that is part of the TGF-β superfamily. A myostatin protein or peptide refers to the full-length unprocessed precursor form of myostatin, as well as any mature peptides or propeptides, or any peptide forms resulting from post-translational processing (e.g., cleavage), or any combinations thereof. Unless otherwise specified as inactive, a myostatin protein or peptide as described herein will retain one or more myostatin biological activities. The term also refers to any fragments and variants of a myostatin protein that maintain at least one biological activity associated with mature myostatin (e.g., myogenesis inhibiting activity), as discussed herein, including sequences that have been modified in any way. The present invention will most typically include human forms of myostatin, or variants thereof, but can include myostatin from any vertebrate species, including, but not limited to, human, bovine, chicken, mouse, rat, porcine, ovine, turkey, baboon, and fish. For non-limiting, exemplary peptide and nucleic acid sequence information, see, e.g., McPherron et al., Proc. Nat. Acad. Sci. U.S.A. 94:12457-12461 (1997); U.S. Pat. No. 7,179,884; each of which is herein incorporated by reference.

Myostatin activity refers to one or more physiologically growth-regulatory or morphogenetic activities associated with active myostatin protein. For example, active myostatin is a negative regulator of skeletal muscle mass and inhibitor of the process of myogenesis. Active myostatin can also modulate the production of muscle-specific enzymes (e.g., creatine kinase), stimulate myoblast proliferation, and modulate preadipocyte differentiation to adipocytes. Myostatin activity includes myostatin binding activity or one or more binding properties of a functionally active myostatin protein. For example, mature myostatin specifically binds to the propeptide portion of myostatin, to ActRIIB, to a myostatin receptor, to activin, to follistatin, to follistatin-domain-containing proteins, to GASP-1, and to other proteins. A myostatin activity increasing agent, such as an antibody or portion thereof, may reduce one or more of these binding activities that would otherwise cause a decrease in myostatin activity. Thus, a myostatin activity increasing agent, in one embodiment, can include an agent that inhibits an inhibitor of myostatin activity. Exemplary procedures for measuring myostatin activity in vivo and in vitro are known in the are and described—see, e.g., U.S. patent application Ser. No. 11/387,643.

A myostatin modulating agent includes any agent capable of modulating myostatin activity in a target tissue. Myostatin activity is as described above, and modulation can include, without limitation, effecting signaling, expression, processing, or secretion of myostatin, or a pharmaceutically acceptable derivative thereof. Agents that either increase or decrease one or more myostatin activities are encompassed by the term. Typically, for purposes of the present invention, agents that increase myostatin activity in a target tissue will be selected for use as described herein. In certain embodiments, a myostatin activity increasing agent will affect binding of myostatin to one or more of its physiological binding partners, including, but not limited to a receptor (e.g. ActRIIB), a follistatin-domain containing protein (e.g. follistatin, FLRG, GASP-1, GASP-2), or a myostatin protein such as the myostatin propeptide and mutants and derivatives thereof Such myostatin activity increasing agents can include, for example, antibodies that specifically bind to an inhibitor of myostatin activity or bind to other proteins that specifically bind to myostatin (such as the myostatin propeptide, mutants and derivatives of the myostatin propeptide, follistatin, follistatin-domain containing proteins, and Fc fusions of these proteins). Myostatin activity increasing agents can include proteins, antibodies, peptides, peptidomimetics, ribozymes, nucleic acids, anti-sense oligonucleotides, double-stranded RNA, siRNA (e.g. for RNAi), small molecules, and various compounds or molecules which specifically increase myostatin activity in a target tissue. Such agents are said to increase or enhance myostatin activity in a target tissue, with the term increased myostatin activity being used in reference to a baseline level of the specified activity (e.g., myogenesis, muscle mass or contractility, etc.), which can include a measurable difference compared to the level of the specified activity in the absence of the agent having the modulating effect.

Thus, in one embodiment, the present invention includes delivering a composition comprising myostatin peptide, or functional fragment thereof, to the target tissue. In such an embodiment, the myostatin peptide or active fragment is considered a myostatin activity increasing agent. The myostatin protein composition can be delivered (e.g., injected, syringe delivered, etc.) directly into the target tissue in order to increase myostatin activity and inhibit myogenesis in the target tissue. Compositions can make use of one or more carriers, stabilizers, physiologically acceptable carriers, suspension media, formulations, and the like and can be delivered to the target tissue by any suitable method (see below).

In yet another embodiment of the present invention, increasing myostatin activity in a target tissue can be accomplished by delivering to the target tissue a polynucleotide encoding a myostatin protein. For example, a myostatin protein or functional fragment can be encoded in a polynucleotide or an expressible polynucleotide, wherein the polynucleotide is contacted with a cell of the target tissue under conditions suitable for introduction of the polynucleotide into the cell and expression of the encoded myostatin protein. The cell into which the expressible polynucleotide is introduced can, but need not be, the target cell (i.e., muscle cell of the target tissue), provided that when the cell is not the target cell, the expressed myostatin protein is secreted, actively or passively, from the cell such that it can contact the target cell and effect its action.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, the polynucleotide can contain nucleoside or nucleotide analogs, or a backbone bond other than a phosphodiester bond. A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Where the polynucleotide encodes a peptide (e.g., myostatin peptide), the coding sequence can be contained in a vector and operatively linked to appropriate regulatory elements, including, if desired, a tissue specific promoter or enhancer, or an peptide tag, expression marker, or any number of other elements. As used herein, the term "operatively linked" or "operatively associated" means that two or more molecules are positioned with respect to each other such that they act as a single unit and effect a function attributable to one or both molecules or a combination thereof. For example, a polynucleotide sequence encoding a myostatin polypeptide can be operatively linked to a regulatory element, in which case the regulatory element confers its regulatory effect on the polynucleotide similarly to the way in which the regulatory element would effect a polynucleotide sequence with which it normally is associated with in a cell. A first polynucleotide coding sequence also can be operatively linked to a second (or more) coding sequence such that a chimeric polypeptide can be expressed from the operatively linked coding sequences.

A polynucleotide useful in performing a method of the invention, can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a polypeptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1: 51-64, 1994; Flotte, J. Bioenerg. Biomemb. 25: 37-42, 1993; Kirshenbaum et al., J. Clin. Invest. 92: 381-387, 1993; each of which is incorporated herein by reference). A tetracycline (tet) inducible promoter is an example of a promoter that can be useful for driving expression of a polynucleotide, wherein, upon administration of tetracycline, or a tetracycline analog, to a subject containing a polynucleotide operatively linked to a tet inducible promoter, expression of the encoded polypeptide is induced.

The polynucleotide also can be operatively linked to tissue specific regulatory element, for example, a muscle cell specific regulatory element, such that expression of an encoded peptide is restricted to muscle cells in target tissue or tissue region of an individual, or a mixed population of cells.

Viral expression vectors can be particularly useful for introducing a polynucleotide into a cell, particularly a target tissue cell in a subject. Viral vectors provide the advantage that they can infect host cells with relatively high efficiency and can infect specific cell types. For example, a polynucleotide encoding a myostatin polypeptide can be cloned into a baculovirus vector, which then can be used to infect an insect host cell, thereby providing a means to produce large amounts of the myostatin. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, BioTechniques 7: 980-990, 1992; Anderson et al., Nature 392: 25-30 Suppl., 1998; Verma and Somia, Nature 389: 239-242, 1997; Wilson, New Engl. J. Med. 334: 1185-1187 (1996), each of which is incorporated herein by reference).

A polynucleotide, which can be contained in a vector, can be introduced into a cell by any of a variety of methods known in the art (Sambrook et al., Molecular Cloning: A laboratory manual (Cold Spring Harbor Laboratory Press 1989); Ausubel et al., Current Protocols in Molecular Biology, John Wiley and Sons, Baltimore, Md. (1987, and supplements through 1995), each of which is incorporated herein by reference). Such methods include, for example, transfection, lipofection, microinjection, electroporation and, with viral vectors, infection/transduction; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as other conditions and desired effects, delivery means, tissue localization, and the like.

A composition of the invention can be prepared for administration to a subject by mixing the myostatin protein or agent with a physiologically acceptable carrier, which is nontoxic in the amount employed. Preparation of such a composition can include combining the myostatin agent with saline, buffers, carriers, stabilizers and the like. Compositions can be maintained, for example, as a suspension or an emulsion, or can be lyophilized, then formulated as desired under conditions such that they are suitably prepared for use in the desired application. As such, the compositions are useful in treating a disorder (e.g., cosmetic disorder, wrinkle, etc.) or for a purpose as disclosed herein. A physiologically acceptable carrier can be any material that, when combined with an a myostatin agent allows the ingredient to retain the desired activity (e.g., biological activity). Examples of such carriers include any of the standard physiologically acceptable carriers such as a phosphate buffered saline solution, water, emulsions such as oil/water emulsion, and various types of wetting agents. Compositions comprising such carriers are formulated by well known conventional methods (see, for example, Remington's Pharmaceutical Sciences, Chapter 43, 14th Ed., Mack Publishing Co., Easton Pa. 18042, USA).

It will be recognized to the skilled clinician that the choice of a carrier, including a physiologically acceptable compound, depends, for example, on the manner in which the compound is to be administered, as well as on the route of administration of the composition. A composition can be administered, for example, intramuscularly, intradermally, or subcutaneously, and also can be administered by injection, topical administration, or other such method known in the art. A composition comprising a peptide or polynucleotide, for example, can be incorporated within an encapsulating material such as into an oil-in-water emulsion, a microemulsion, micelle, mixed micelle, liposome, microsphere or other polymer matrix (see, for example, Gregoriadis, Liposome Technology, Vol. 1 (CRC Press, Boca Raton, Fla. 1984); Fraley, et al., Trends Biochem. Sci., 6: 77, 1981, each of which is incorporated herein by reference).

In another embodiment of the present invention, increasing myostatin activity in a target tissue, according to methods of the invention, can be used in conjunction with other treatment techniques and methodologies. For example, methods of increasing myostatin activity in a target tissue can be utilized in conjunction with other cosmetic treatments, such as wrinkle alleviation treatments.

Figure 2:
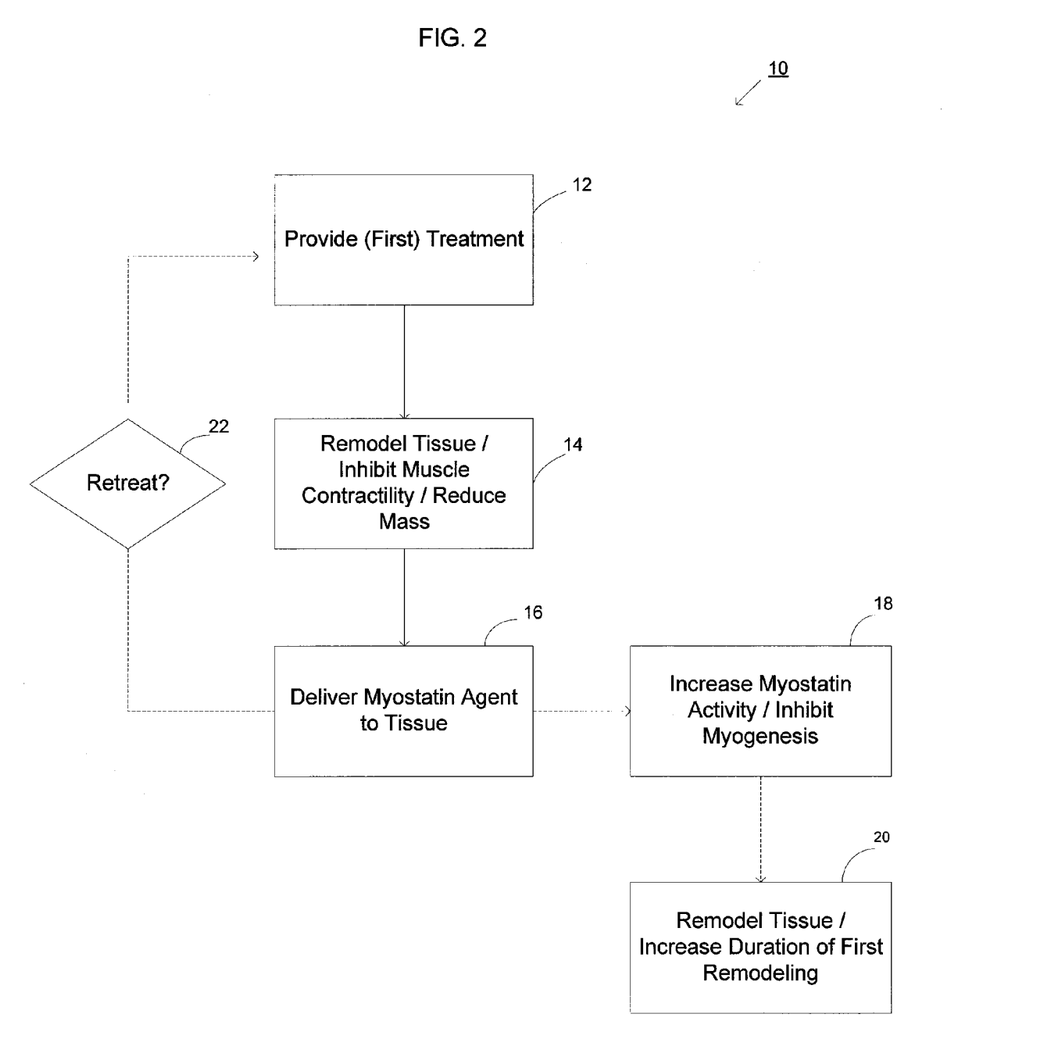
FIG. 2 is a flowchart schematically illustrating a method for cosmetically treating a target tissue, according to an embodiment of the present invention.

FIG. 2 provides a flowchart illustrating a method 10 of treating a target tissue of a patient, according to an embodiment of the present invention. A first treatment (e.g., wrinkle alleviation treatment) can be provided to the patient (Step 12). The treatment will be selected to at least partially remodel the target tissue so as to alter the surface of the skin, and treatment can include inhibiting contraction or contractility of muscles (e.g., subdermal muscles) that cause a irregularity or wrinkle in the surface of the skin (Step 14). Next, an agent is delivered to the target tissue so as to increase myostatin activity in the target tissue (Step 16). Myostatin activity in the target tissue is increased, which can inhibit myogenesis in the cells (muscle cells) of the target tissue (Step 18). The increased myostatin activity can further remodel the target tissue, e.g., further inhibiting muscle contractility, reducing muscle mass, and/or increase the duration of the effects of the first treatment of Step 12 (Step 20).

The process can optionally be repeated at any point (Step 22). In one embodiment, as illustrated, myostatin agent can be delivered following an initial (e.g., "first") treatment, though order can optionally be reversed, or delivered substantially at the same time.

One such method that can be used in conjunction with myostatin activity increasing techniques described herein is application or delivery of cryogenic cooling to a target tissue. Thus, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., optionally so as to provide a permanent treatment that limits or avoids inflammation and mobilization of skeletal muscle satellite repair cells. Apoptosis also may be induced using treatment temperatures below about −15° C., including temperatures from about −1° C. to about −20° C. Hence, the duration of the treatment efficacy of such subdermal cryogenic treatments may be selected and controlled, with colder temperatures, longer treatment times, and/or larger volumes or selected patterns of target tissue determining the longevity of the treatment. Non-limiting exemplary systems and techniques for cryogenic cooling of target tissues that can be employed in the present invention are further described, for example, in commonly owned, co-pending applications U.S. application Ser. No. 11/295,204; U.S. application Ser. No. 11/770,185; U.S. application Ser. No. 11/614,887; U.S. application Ser. No. 11/675,886, the full disclosures of which are incorporated herein by reference.

Figure 3:
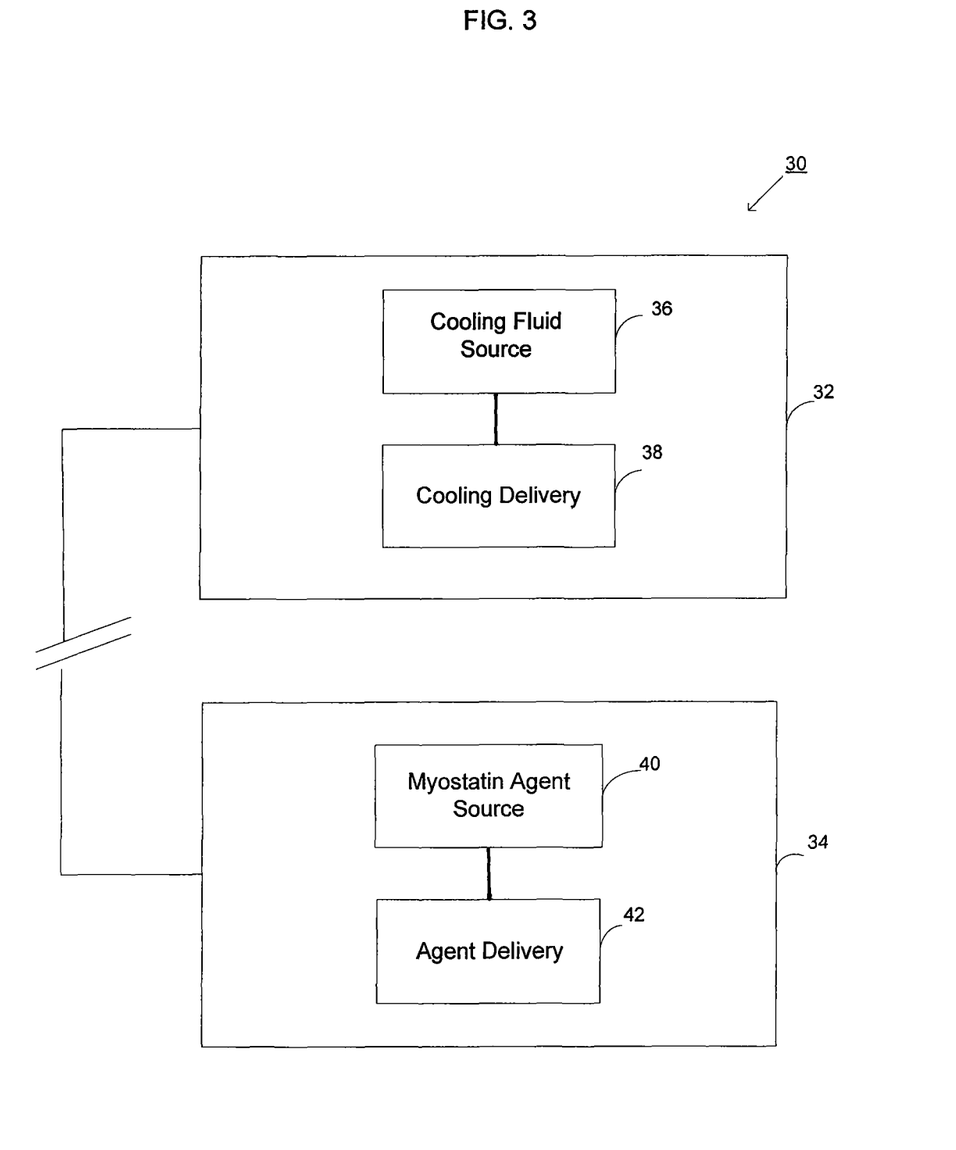
FIG. 3 is a block diagram graphically illustrating components of a system according to one embodiment of the present invention.

Referring to FIG. 3, a system 30 for providing treatment to a patient with a combination of tissue cooling and increasing myostatin activity in a target tissue is described. The system includes a target tissue cooling unit 32 and a myostatin agent delivery unit 34. The cooling unit 32 will typically include a cooling fluid source 36 that can be coupled to a delivery means 38 for delivering cooling to the target tissue. Various cooling delivery structures can be utilized according to the present invention, e.g., as described further herein, and, in one embodiment, can include a probe, such as a needle-like probe with a tissue piercing portion (e.g., tissue piercing distal end). Such a probe can be coupled to the source 36 such that the probe is in thermal communication with the source. The myostatin agent delivery unit 34 can include a source 40 for a myostatin activity increasing agent (e.g., see above) and a means 42 for delivering the agent or myostatin composition to the target tissue. Delivery of a myostatin agent or composition can include a variety of methodologies and/or structures, as described further herein, including, for example, injection of a composition into the target tissue, topical administration, vector compositions, and the like.

Figure 4A:
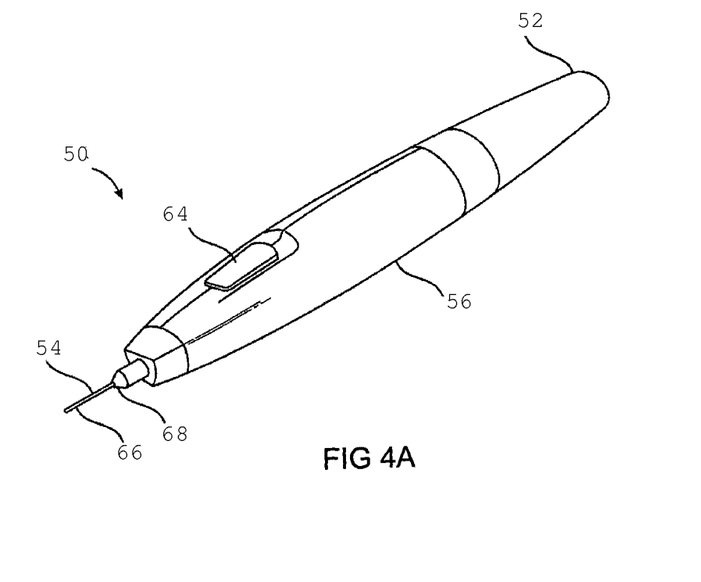
FIG. 4A is a perspective view of a self-contained subdermal cryogenic remodeling probe and system, according to an embodiment of the invention.
Figure 4B:
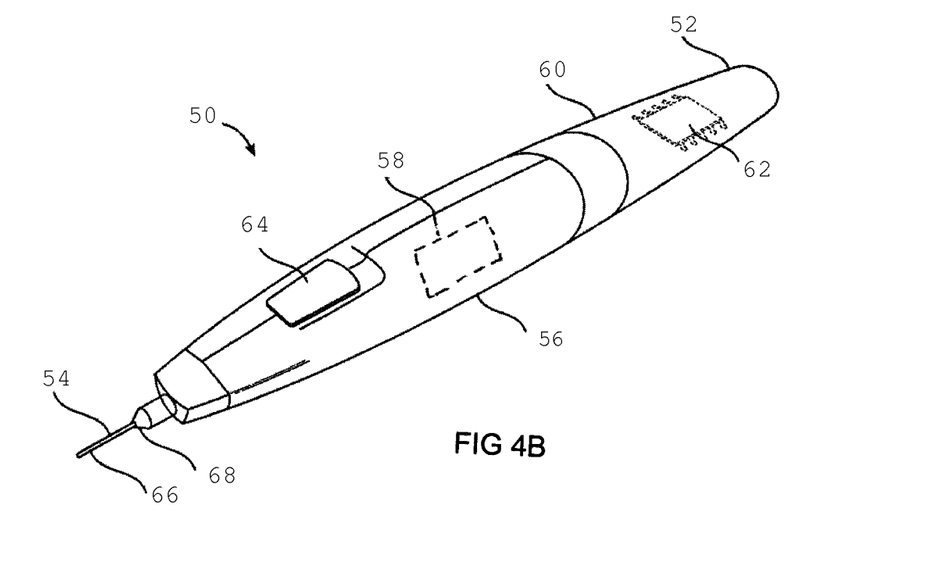
FIG. 4B is a partially transparent perspective view of the self-contained probe of FIG. 4A, showing internal components of the cryogenic remodeling system.

Referring now to FIGS. 4A and 4B, an exemplary system for subdermal cryogenic remodeling that can be employed for use in the present invention is described. The system 50 comprises a self-contained probe handpiece generally having a proximal end 52 and a distal end 54. A handpiece housing 56 has a size and shape suitable for supporting in a hand of a surgeon or other system operator. As can be seen most clearly in FIG. 4B, a cryogenic cooling fluid supply 58 and electrical power source 60 are found within housing 56, along with a circuit 62 having a processor for controlling cooling applied by self-contained system 10 in response to actuation of an input 64.

Extending distally from distal end 54 of housing 56 is a tissue-penetrating cryogenic cooling probe 66. Probe 66 is thermally coupled to a cooling fluid path extending from cooling fluid source 58, with the exemplary probe comprising a tubular body receiving at least a portion of the cooling fluid from the cooling fluid source therein. The exemplary probe 66 comprises a 30 g needle having a sharpened distal end that is axially sealed. Needles of various sizes can be included in the present invention and can include needles smaller than 20 g needles, as well as embodiments with needles sized from 14 g to 32 g. Probe 66 may have an axial length between distal end 54 of housing 56 and the distal end of the needle of between about ½ mm and 5 cm, preferably having a length from about 1 mm to about 3 mm, and from about 1 cm to about 3 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches.

Additionally, while needles are generally illustrated herein as being straight or substantially linear, needles suitable for use in the present invention can include a variety of shapes and configurations. For example, needles can be curved or comprise a curved portion, including pre-bent or curve-shaped needles, and the like. Also, while a needle or probe 66 will generally extend distally from the distal end 54 of the housing, the positioning of the probe is not limited to any particular orientation and can, for example, extend substantially along a long axis of the housing 56, or the probe 66 can be at an angle relative to the long axis. Particular shape and/or configuration or orientation of the probe 66 may depend at least partially on the intended use of the device, as certain probe shapes, configurations, and/or orientations may be desired for particular treatments or probe positioning within a target tissue.

Addressing some of the components within housing 56, the exemplary cooling fluid supply 58 comprises a cartridge containing a liquid under pressure, with the liquid preferably having a boiling temperature of the less than 37° C. When the fluid is thermally coupled to the tissue-penetrating probe 66, and the probe is positioned within the patient so that an outer surface of the probe is adjacent to a target tissue, the heat from the target tissue evaporates at least a portion of the liquid and the enthalpy of vaporization cools the target tissue. A valve (not shown) may be disposed along the cooling fluid flow path between cartridge 58 and probe 66, or along the cooling fluid path after the probe so as to limit the temperature, time, rate of temperature change, or other cooling characteristics. The valve will often be powered electrically via power source 60, per the direction of processor 62. The exemplary power source 60 comprises a rechargeable or single-use battery.

The exemplary cooling fluid supply 58 comprises a single-use cartridge. Advantageously, the cartridge and cooling fluid therein may be stored and/or used at (or even above) room temperature. The cartridges may have a frangible seal or may be refillable, with the exemplary cartridge containing liquid $N_2O$. A variety of alternative cooling fluids might also be used, with exemplary cooling fluids including fluorocarbon refrigerants and/or carbon dioxide. The quantity of cooling fluid contained by cartridge 58 will typically be sufficient to treat at least a significant region of a patient, but will often be less than sufficient to treat two or more patients. An exemplary liquid $N_2O$ cartridge might contain, for example, a quantity in a range from about 7 g to about 30 g of liquid. Other embodiments can include liquid $N_2O$ cartridge in a quantity less than about 7 g, including embodiments designed for a smaller limited amount of use or even single use.

Processor 62 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 62 may be integrated on a single processor board and may run a single program or may make use of a plurality of boards running a number of different program modules in a wide variety of alternative distributed data processing or code architectures.

It will be noted that systems and devices of the present invention can make use of a variety of power sources including, for example, an on-board power sources, such as a battery that can provide for a more portable and/or maneuverable, as well as self-contained, system or device. In one embodiment, for example, a power source 60 (e.g., battery) can be positioned in and/or affixed to the handpiece housing 16 or otherwise coupled with the housing 56 in a manner such that the probe device, including the needle probe 66, battery or power source 60, as well as other components, can be manipulated and positioned my manipulation of the handpiece housing 56.

Besides cryogenic tissue cooling techniques, including those described above, other wrinkle alleviation and/or cosmetic treatment methods will find use in the present inventive methods. One such treatment that can be provided according to the current methods, which is commonly used for cosmetic treatment of skin surface alterations and wrinkles, includes BOTOX™ (botulinum neurotoxin A) treatment techniques. Currently, BOTOX™ is a popularly used neurotoxin is used to temporarily eliminate muscle movement in the face for cosmetic aesthetics. Botox has also been used off label for therapeutic treatments which has led to serious adverse events which include death (Cote T R, Mohan A K, Polder J A, Walton M K, Braun M M. J. Am. Acad. Dermatol. 53: 407-15 (2005)). Other non-limiting examples of cosmetic treatment methods and/or wrinkle alleviation techniques include application of other forms of energy delivery, including radiofrequency (e.g., RF ablation), ultrasound energy, and the like, as well as various surgical treatments and methodologies.

Figure 5:
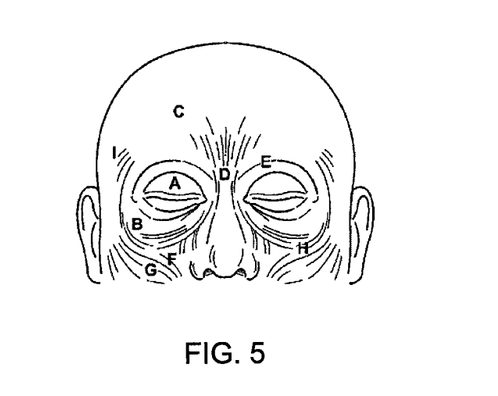
FIG. 5 and FIGS. 5A-5L illustrates target tissues for treatment in some embodiments of the present invention, along with associated lines or wrinkles and treatment patterns.
Figure 5A:
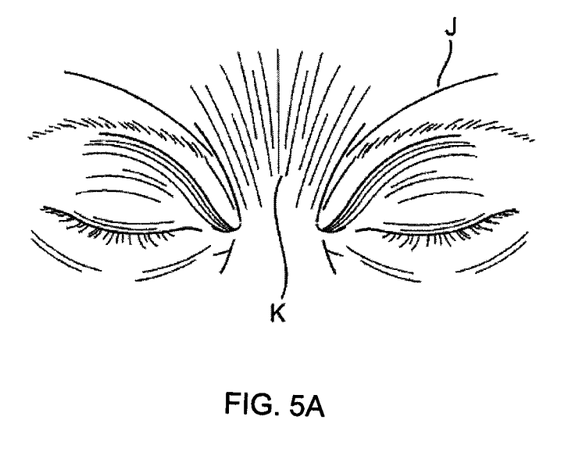
Figure 5B:
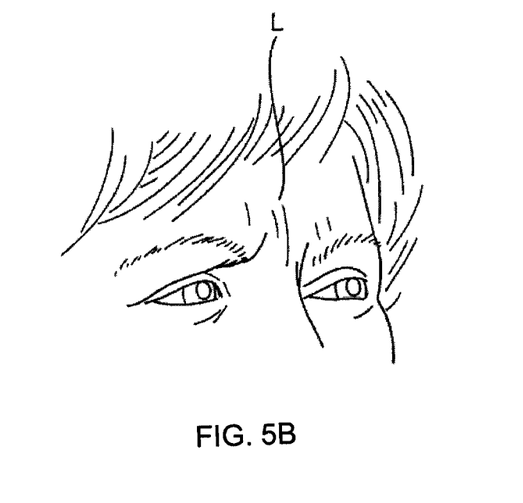
Figure 5C:
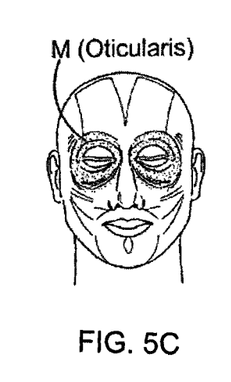
Figure 5D:
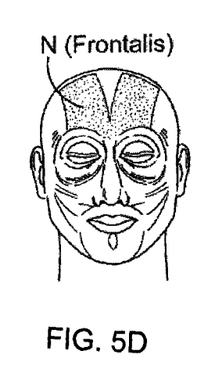
Figure 5E:
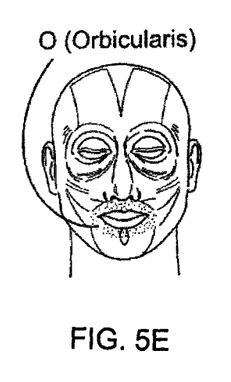
Figure 5F:
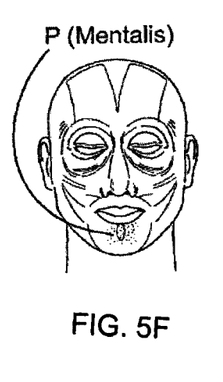
Figure 5G:
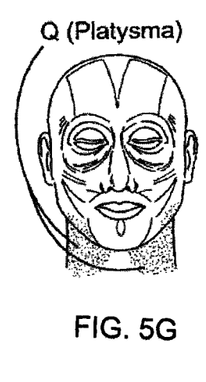
Figure 5H:
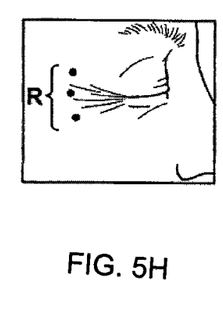
Figure 5I:
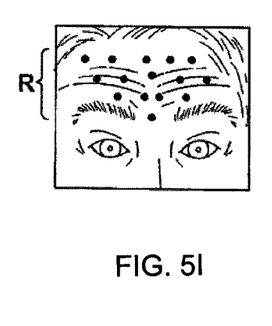
Figure 5J:
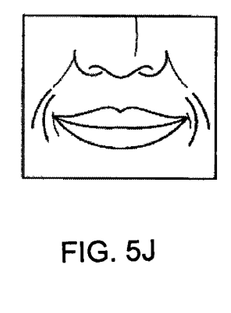
Figure 5K:
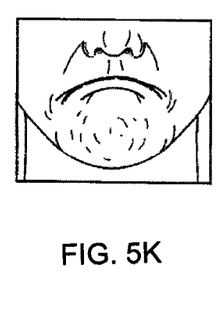
Figure 5L:
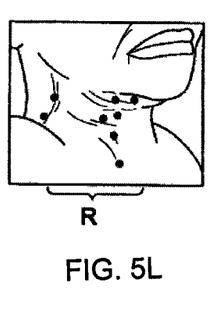
Figure 5M:
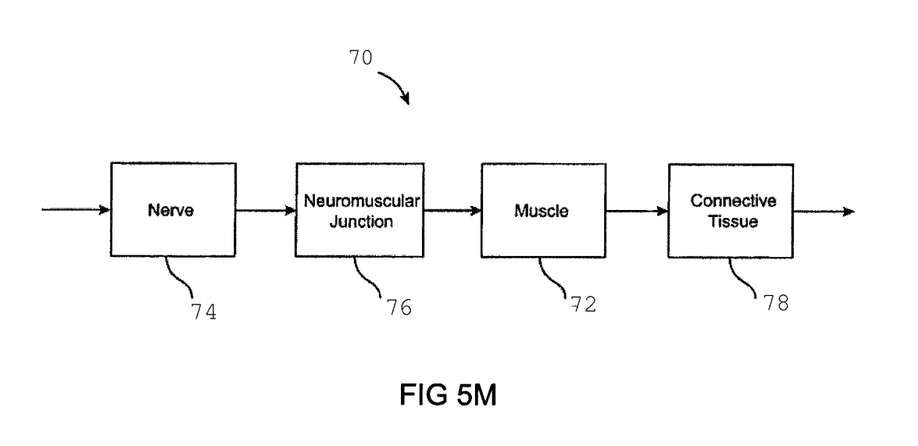
FIG. 5M is a functional block diagram graphically illustrating tissue components included in a contractile chain.

As indicated above, among the most immediate applications of the present invention may be the amelioration of lines and wrinkles, particularly by inhibiting muscular contractions which are associated with these cosmetic defects so as to improve an appearance of the patient. Referring now to FIGS. 5 through 5M, subdermal remodeling of tissues for alleviation of lines and wrinkles will find particular applications for skin surface regions of the face and neck, with procedures optionally being performed so as to alter contractile function of muscles A-I in the upper one-third of the face as shown in FIG. 5. Treatments may be performed so as to alleviate frown lines, lines or wrinkles between the eyes, crow's feet, horizontal lines in the forehead, neck, wrinkles around the mouth, chin, and the like. Many of these cosmetic defects may be treated by targeting and/or inactivating tissues such as the corrugator and/or procerus muscles. More specifically, as seen in FIGS. 5A and 5B, movement of the facial muscles can cause the skin to crease, for example, with contraction of corrugator muscle J and/or procerus muscle K leading to creases between the brows L, which may be clinically referred to as glabellar lines. Additional treatment locations, muscles M-Q whose contractile function may be targeted, related lines or wrinkles, and treatment patterns R are illustrated in FIGS. 5C-5L.

Regarding the specific muscles and tissue structures identified in FIG. 5, treatments may be directed towards one or more of levator palpebrae superioris A, orbicularis oculi B, frontalis C, levator labii D, corrugator E, zygomaticus minor F, zygomaticus major G, buccinator H, and/or temporalis I. Treatments targeting contraction of oticularis M of FIG. 5C may help decrease crow's feet wrinkles of FIG. 5H, optionally using a treatment pattern R. Treatments altering the function of Frontalis N of FIG. 5D may alleviate the wrinkles of FIG. 5I, while altering functioning of Orbicularis O of FIG. 5E may alleviate the wrinkles shown in FIG. 5J. Wrinkles of the chin as shown in FIG. 5K may be mitigated by treatment of Mentalis P and neck wrinkles such as those of FIG. 5L may be improved by treatments of platysma Q, as seen in FIG. 5G. Treatment patterns R for improvement of these and other cosmetic defects may correspond to or be derived from known treatments (such as patterns for injections of BOTOX® or the like), may be determined by anatomical analysis using the desired physiological effects, by animal or clinical studies, or the like.

Target muscles for contraction inhibition so as to alleviate wrinkles and the like may often include the glabellar and procerus complex including, but not limited to, the corrugator procerus, orbicularis oculi, depressor, supercilli, and frontalis. Other muscle groups of the facial region may also be contraction-inhibited, such as the nasalis, orbicularis oris, buccinator, depressor anguli oris, quadratus labii superioris and inferioris, zygomaticus, maxillae, platysma, and mentalis. Contraction of these and/or other muscles may be inhibited by targeting associated nerve tissues, connective tissues, nerve/muscle interface, blood supply, and/or at least a portion of tissues of one or more of these muscles themselves. Preferred wrinkle alleviation treatments may alter functioning of muscles including one or more of, but not limited to, frontalis pars medialis, frontalis pars lateralis, corrugator supercilii, procerus, depressor supercilii, levator palpebrae superioris, orbicularis oculi pars orbitalis, orbicularis oculi pars palpebralis, levator labii superioris alaquae nasi, levator labii superioris, zygomaticus minor, zygomaticus major, levator anguli oris (a.k.a. caninus), buccinator, depressor anguli oris (a.k.a. triangularis), depressor labii inferioris, mentalis, incisivii labii superioris, incisivii labii inferioris, risorius, platysma, orbicularis oris, masseter, temporalis, internal pterygoid, digastric, nasalis, maxillae, quadratus labii superioris and inferiors.

In many embodiments, remodeling a tissue included in a contractile function chain 70 will effect a desired change in a composition of the treated tissue and/or a change in its behavior which is sufficient to mitigate wrinkles of the skin associated with contraction of a muscle 72, as illustrated in FIG. 5M. While this may involve a treatment of the tissues of muscle 72 directly, treatments may also target nerve tissues 74, neuromuscular junction tissues 76, connective tissues 78, and the like. Still further tissues may directly receive the treatment, for example, with treatments being directed to tissues of selected blood vessels so as to induce hypoxia in muscle 72 or the like. Regardless of the specific component of contractile chain 70 which is treated, the treatment will preferably inhibit contraction of the muscle 72 which would otherwise form wrinkles or lines in the exposed skin surface overlying that muscle.

A variety of specific tissue remodeling treatments mechanisms targeting of one or more components of contractile chain 70 may be employed so as to inhibit lines or wrinkles. For example, ablation of muscle cells/tissues, or the associated nerves (optionally being a component thereof integral to nerve function such as a myelin sheath or the like), or the nerve endings or neuromuscular junction (which generally forms the interface between the nerves and the muscles) may be sufficient to inhibit muscular contraction. Such ablation may result in a short-term, long-term or permanent inactivation of the muscle. Other long-lasting or permanent treatments may involve inducing apoptosis, typically at temperatures which are not as severe as ablation temperatures, but which remodel the tissue behavior with long term changes in the cellular life and/or proliferation cycles. Specific remodeling mechanisms so as to change the function of the muscle in a desired way or for a desired time may be induced by appropriate therapeutic dosages of the treatment modalities described herein, for example so as to induce cell death (apoptotic or necrotic), embolization of blood supply, or the like. Alternative remodeling mechanisms which may be shorter in effect may include stunning of one or more component of contractile chain 70, inactivation of one or more component, or the like. Remodeling treatments which effectively block the release of or response to chemicals (such as but not limited to acetylcholine) along the contractile chain 70 may be sufficient to inhibit muscular contraction in response to signals transmitted along the neural pathways, either temporarily or permanently, and may also be employed.

Muscular movement is generally controlled by stimulation of a nerve. The motor unit of the neuromuscular system contains three components: motor neuron (spine), axon (spine to motor endplate), and innervated muscle fibers (endplate to muscle). Treatments directed to one or more of these tissues may be employed.

When treatments are intended to inhibit muscle contraction, the treatment may be determined at least in part by the type of muscle being treated (skeletal (striated) or smooth (not striated)). For example, skeletal muscle may have muscle fibers that are innervated by motor neuron, with a single neuromuscular junction lying along a midpoint of muscle fibers, and a single muscle fiber within a motor unit supplied by a single motor neuron and its axon. Each muscle receives one or more nerves of supply, and the nerve generally enters deep into the muscle surface near its origin where the muscle is relatively immobile. Blood vessels typically accompany the nerve to enter the muscle at the neurovascular hilum. Each nerve contains motor and sensory fibers, motor endplates, vascular smooth muscle cells, and various sensory endings and endings in fascia. When the nerve enters the muscle, it breaks off into a plexus running into the various layers of muscle—epimysium, perimysium, endomysium—each terminating in several branches joining a muscle fiber at the motor endplate. Remodeling of one or more of these tissues may be sufficient to temporarily or permanently inhibit muscle contraction.

Embodiments of the invention may interrupt or disable nerve impulses by disrupting conductivity by eliminating or decreasing charge differences across plasma membranes, either mechanically or chemically; by destroying Schwann cells that insulate the axonal processes speeding up impulse conduction; and/or by repeated injury/healing cycles timed to limited capacity for neuron regeneration.

Immobilization of muscle by disabling any one or a specified combination of components of the connective tissue matrix, either temporarily or permanently, may also be employed. Treatments targeting connective tissues, such as the fibroblasts, myofibroblasts (which may be responsible for contractility of granulation tissue in healing), collagen, reticulin, elastin, or the like of aponeurotic or tendinous attachment of muscles to bone, fascia, ligaments, or the like may also be advantageous, and the remodeling form and/or treatment dosage may be selected in response to the condition being treated (for example, when primarily treating cellulite dimples rather than primarily treating contraction-induced lines or wrinkles). Treatments of the superficial fascia just beneath the skin may also be employed. To achieve a loss of elasticity in fibrous connective tissue during treatment of cellulite, temperature may be varied to achieve temporary or permanent changes to the morphology of the collagen and elastin matrix contained within that tissue.

In addition to cosmetic treatments of lines, wrinkles, and the like, embodiments of the invention may also find applications for treatments of subdermal adipose tissues. Embodiments of the invention may also find applications for alleviation of pain, including those associated with muscle spasms. Still further embodiments may rely on application of energy (with or without cooling) for remodeling of target tissues and producing a desired cosmetic effect, with the energy optionally comprising focused or unfocused ultrasound energy, radio frequency energy, laser energy microwave energy, other electromagnetic or particle radiation, alternative methods of applying heat, chemicals, vascular embolization, and the like. Hence, a variety of embodiments may be provided. In one embodiment, for example, delivery of energy, such as radio frequency energy, can be used to target and disable muscle tissue of the target tissue as opposed to targeting nerve ablation to block competition.

Figure 6:
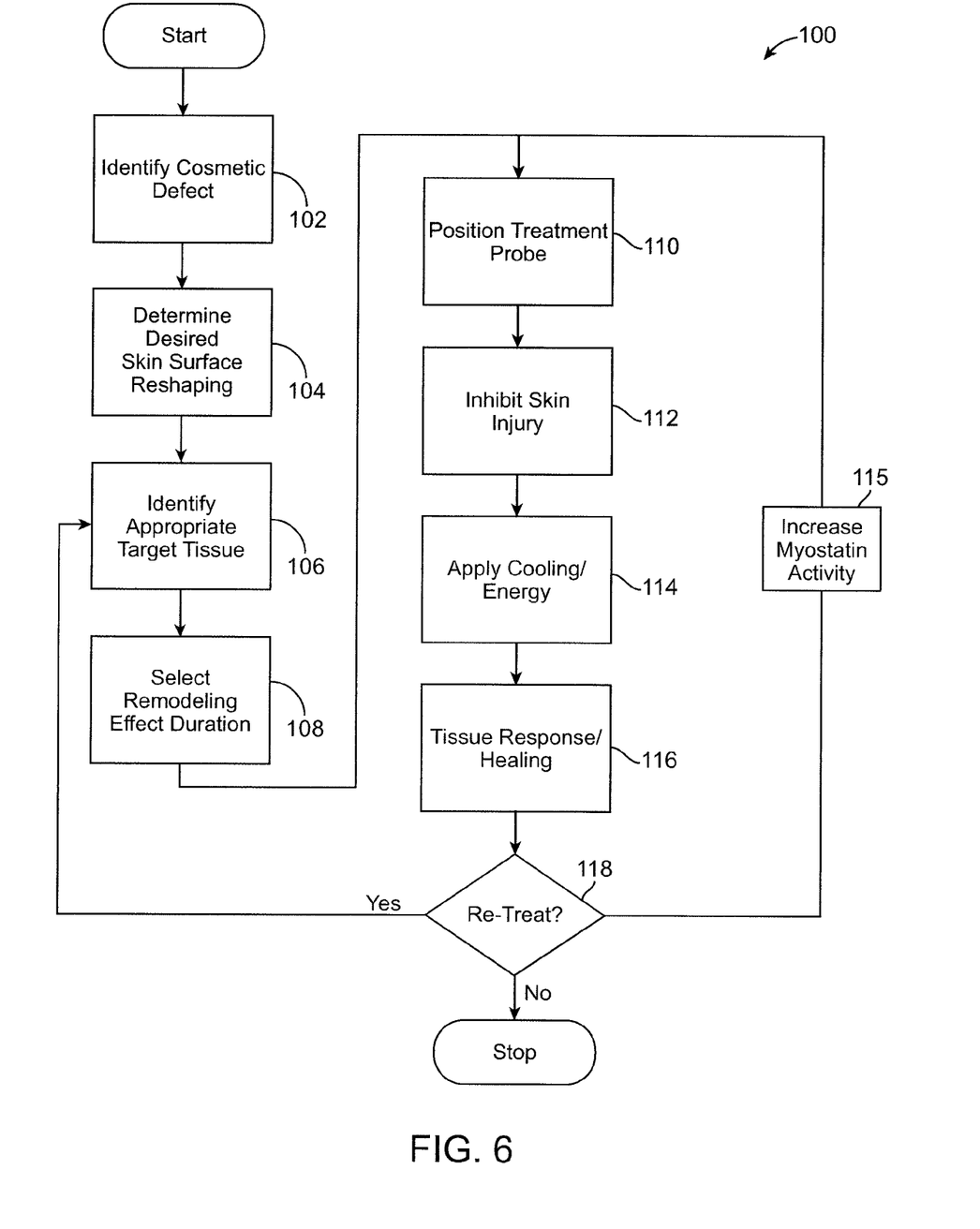
FIG. 6 is a flowchart schematically illustrating a method for cosmetically treating a target tissue disposed below a skin surface using both cryogenic cooling and increasing of myostatin activity so as to reshape the skin surface.

Referring now to FIG. 6, an embodiment of a method 100 for effecting a cosmetic treatment 100 includes identifying a cosmetic defect 102 such as lines, wrinkles, cellulite, fat, or the like. A desired skin surface reshaping is determined 104 which may include the elimination of lines or wrinkles, smoothing of cellulite dimples, reduction of fat, or the like. In many embodiments, it may be desirable to avoid permanently altering a color of the skin surface in effecting such treatments.

An appropriate target tissue is identified 106, such as identifying a nerve, muscle, neuromuscular junction, connective tissue, adipose tissue layer, or the like below the cosmetic defect. A remodeling effect duration 108 may be selected, and the treatment probe positioned 110. Positioning of the treatment probe may, for example, comprise inserting one or more tissue-penetrating probe needles into the target tissue, engaging the skin surface with a skin-engaging surface of a handpiece, and/or the like. Injury to the skin may be inhibited 112, such as by warming the skin surface, infusing a warmed biocompatible fluid such as saline, applying a cryoprotectant such as DMSO, or the like.

Cooling and/or energy (or chemical or vascular embolization) is applied to the target tissue 114 so as to effect the desired remodeling of that tissue. The tissue response and healing 116 may follow immediately after cooling and/or energy (or chemical or vascular embolization) is applied, or may take place over a considerable time (such as when efficacy is achieved through apoptosis or the like). Furthermore, a step is included where myostatin activity in the target tissue in increased 115, e.g., by delivery of a myostatin agent (e.g., myostatin protein) to the target tissue. The increased myostatin activity can act to further remodel the target tissue in the desired manner, and/or can extend the duration of the cosmetic defect correction actions of the tissue cooling compared to cooling alone. The increased myostatin activity, for example, can effectively inhibit certain aspects of the healing response, such as myogenesis. Delivery of the myostatin agent can be accomplished before, after or concurrently with application of the tissue cooling. Generally, for certain myostatin agents, such as myostatin protein, delivery of the agent will occur before, and typically after, application of tissue cooling, as cooling can in some instances effect biological activity of the agent. In some instances, e.g., if a short duration or trial treatment was performed to verify the target tissue and treatment effect, retreatment 118 may optionally be performed.

Permanent and/or temporary muscular function inhibition may be employed. A temporary effect can be used on a trial basis to avoid long term injuries or undesirable outcomes. A permanent effect may be desirable to minimize cost and avoid repeated treatments. Desired temperature ranges to temporarily and/or permanently disable muscle, as well as protect the skin and surrounding tissues, may be indicated by Table 1 as follows:

TABLE 1

| Temperature | Skin | Muscle/Fat |
|---|---|---|
| 37° C. | baseline | baseline |
| 25° C. | cold sensation | |
| 18° C. | reflex vasodilation of deep blood vessels | |
| 15° C. | cold pain sensation | |
| 12° C. | reduction of spasticity | |
| 10° C. | very cold sensation reduction of chronic oedema Hunting response | |
| 5° C. | pain sensation | |
| 0° C. | freezing point | |
| −1° C. | | Phase transition begins |
| −2° C. | | minimal apoptosis |
| −3° C. | | Peak phase transition |
| −5° C. | tissue damage | moderate apoptosis |
| −8° C. | | Completion of phase transition |
| −10° C. | | mild apoptosis; considerable apoptosis |
| −15° C. | | moderate apoptosis; extensive apoptosis mild-moderate necrosis |
| −40° C. | | extensive necrosis |

It will be recognized that the methods of the present invention can be directed to a variety of target tissues and are not limited to any particular tissue. Target tissues amenable to treatment according to the present invention can include without limitation, for example, tissues that have been subjected to cryogenic or cryosurgical treatments using previously known techniques for delivering cooling energy to tissues (e.g., open spray, touch probe). See, e.g., *Cutaneous Cryosurgery: Principles and Clinical Practice* (3rd Edition); Jackson et al., CRC Press, 2005. Target tissues can typically include dermatological tissues and/or subcutaneous tissues. For example, a target tissue can include a patient's skin, including an outer surface of the patient's skin as well as tissues of the skin located below the skin surface. In one embodiment, for example, a needle probe can be advanced distally so as to penetrate into the patients skin, e.g., through a surface of the skin and cooling energy directed to the skin surface and/or to tissue below the skin, including tissues at various depths of penetration into or through the skin surface and into or through the skin tissue itself.

As set forth above, target tissues can include skin, muscles or muscle containing tissues, nerves, connective tissue, as well as adipose tissues. Target tissues can also include various types of lesions, wounds, and the like. Target tissues can include cancerous lesions, malignant or premalignant lesions, or tissues having cells either exhibiting or predisposed to exhibiting unregulated growth. Target tissues can additionally include benign lesion. Non-limiting examples of benign lesions amenable to treatment according to the present invention can include the following: acne; adenoma sebaceum; alopecia areata; angiokeratoma; angiolymphoid hyperplasia; cherry angioma; chondrodermatitis nodularis helices; clear cell acanthoma; cutaneous horn; dermatofibroma; dermatosis papulosa nigrans; disseminated superficial actinic keratosis; elastosis perforans serpiginosa; epidermal naevus; granuloma annulare; granuloma faciale; haemangioma; herpes labialis, recurrent; hidradenitis suppurativa; hyperhidrosis, axillary; hypertrophic scar; idiopathic guttate melanosis; ingrowing toenail; keloid; kyrle's disease; leishmaniasis; lentigines; lentigo simplex; lichen planus, hypertrophic; lichen sclerosus, vulva; lichen simplex; lichenoid keratosis, benign; lupus erythematosus, discoid; lymphangioma; lymphocytoma cutis; melasma; milia; molluscum contagiosum; mucocoele, mouth; myxoid cyst, digital; orf; pigmented naevi; porokeratosis; prurigo nodularis; pruritus ani; psoriasis, lichenified; pyogenic granuloma; rhinophyma; rosacea; sarcoid, granuloma; sebaceous hyperplasia; seborrhoeic keratosis; skin tags; solar atropy, keratosis, or lentigo; spider naevus; steatocystoma multiplex; syringoma; tattoos; trichiasis; trichoepithelioma; venous lakes; warts; or xanthoma.

In some instances it may be desired to cool the target tissue, as described above, but without penetrating the target tissue with a cooling probe. As such, according to another embodiment, delivery of the cooling energy to the target tissue can be accomplished using a non-penetrating probe. Rather than penetrating into the target tissue as with a needle electrode, the non-penetrating probe is positioned in contact with a portion of the target tissue (e.g., skin surface), and cooling is directed through the probe and the cooling transferred to the target tissue. The probe includes at least one tissue engaging surface that is positioned in contact with the target tissue for tissue cooling. Systems and devices of the present invention having the non-penetrating probe configuration can be used, for example, for treating a target tissue comprising a lesion, such as an acne lesion. Similar to the above, tissue cooling in this manner can be used for treating and remodeling the acne lesion target tissue, for example, by stimulating apoptosis, reducing or eliminating infection or inflammation, reduction in scarring, and the like.

It is understood that the examples and embodiments described herein are for illustrative purposes and that various modifications or changes in light thereof may be suggested to persons skilled in the art and are to be included within the spirit and purview of this application and the scope of the appended claims. Numerous different combinations are possible, and such combinations are considered to be part of the present invention.

What is claimed is:

1. A method of augmenting cosmetic effects of wrinkle reduction treatment, the method comprising administering an agent at a treatment site on or below the skin,
    wherein the agent comprises a myostatin protein or a functional fragment thereof;
    whereby the agent modulates myoblasts so as to inhibit myogenesis, thereby inhibiting lines or wrinkles and effectively smoothing the skin at or around the treatment site.

2. The method of claim 1, wherein the agent causes weakening or reduction in mass of sub-dermal muscle.

3. The method of claim 1, wherein the agent comprises a myostatin protein.

4. The method of claim 1, wherein the method further comprises inhibiting follistatin activity in the target tissue.

5. The method of claim 4, wherein inhibiting follistatin activity comprises delivering a follistatin binding agent to the target tissue.

6. The method of claim 5, wherein the follistatin binding agent comprises an antibody.

7. The method of claim 1, further comprising providing a further wrinkle alleviation treatment to the target tissue comprising delivery of cryogenic cooling, radiofrequency energy, botulinum toxin, surgical treatment, or a combination thereof.

8. The method of claim 7, wherein the wrinkle alleviation treatment is provided to the patient prior to administering the agent to the target tissue.

9. A method of treating skin of a patient, comprising;
    (a) cooling tissue underneath the skin using a probe inserted through the skin at a treatment site; and
    (b) delivering myostatin protein or a functional fragment thereof to tissue underneath the skin at or around the treatment site;
    whereby the treating inhibits lines or wrinkles and effectively smoothes the skin at or around the treatment site.

10. The method of claim 9, wherein the cooling is selected to induce muscle tissue damage and decrease muscle contractility in the target tissue.

11. The method of claim 9, wherein the myostatin or fragment inhibits myogenesis in the target tissue.

12. The method of claim 9, wherein the myostatin or fragment prolongs the skin shape alteration provided by the cooling of the target tissue.

13. A method for treating a target tissue that is below the skin of a patient, the method comprising:
    (a) inserting a needle probe distally to penetrate into the target tissue;
    (b) cooling the target tissue by way of the probe; and
    (c) administering an agent at or around the treatment site, wherein the agent comprises a myostatin protein or a functional fragment thereof;
    whereby treating the target tissue according to the method inhibits lines or wrinkles on a surface of the skin adjacent to a portion of the target tissue, thereby effectively smoothing the surface of the skin.

14. The method of claim 13, wherein the cooling causes at least temporary denaturation of proteins of the muscle tissue.

15. The method of claim 13, wherein the cooling is selected so as to modulate calcium signaling in the muscle of the target tissue, thereby disrupting or inhibiting contractile function of the muscle.

16. The method of claim 13, wherein the cooling is selected so as to induce ice formation and a hypertonic environment in at least a portion of the target tissue.

17. The method of claim 16, wherein the induction of ice formation comprises freezing of extracellular fluid in the target tissue so as to induce a cellular response in the target tissue.

18. The method of claim 13, wherein the cooling disrupts electrical signaling or recruitment of a motor unit of the muscle of the target tissue.

19. The method of claim 9, wherein the myostatin or fragment is administered before or concurrently with the cooling.

20. The method of claim 9, wherein the myostatin or fragment is administered after the cooling.

21. The method of claim 1, wherein the agent is injected subcutaneously.

22. The method of claim 1, wherein the agent is administered topically.

* * * * *